(12) United States Patent
Thyzel

(10) Patent No.: US 10,406,031 B2
(45) Date of Patent: Sep. 10, 2019

(54) APPLICATOR AND DEVICE FOR CELL TREATMENT

(71) Applicant: A.R.C. Laser GmbH, Nuremberg (DE)

(72) Inventor: Reinhardt W. F. Thyzel, Eckental (DE)

(73) Assignee: A.R.C. Laser GmbH, Nuremberg (DE)

( * ) Notice: Subject to any disclaimer, the term of this patent is extended or adjusted under 35 U.S.C. 154(b) by 1512 days.

(21) Appl. No.: 13/935,086

(22) Filed: Jul. 3, 2013

(65) Prior Publication Data

US 2014/0012186 A1    Jan. 9, 2014

(30) Foreign Application Priority Data

Jul. 5, 2012   (DE) .................. 10 2012 106 017

(51) Int. Cl.
| | |
|---|---|
| *A61F 9/008* | (2006.01) |
| *A61B 18/26* | (2006.01) |
| *A61B 18/04* | (2006.01) |
| *A61F 9/007* | (2006.01) |

(Continued)

(52) U.S. Cl.
CPC ............ *A61F 9/008* (2013.01); *A61B 18/042* (2013.01); *A61B 18/26* (2013.01); *A61F 9/00736* (2013.01); *A61F 9/00825* (2013.01); *A61B 2018/0047* (2013.01); *A61B 2018/00458* (2013.01); *A61B 2018/00577* (2013.01); *A61B 2018/2005* (2013.01); *A61B 2018/266* (2013.01); *A61F 2009/0087* (2013.01); *A61F 2009/00887* (2013.01)

(58) Field of Classification Search
CPC .. A61F 9/008; A61F 9/00736; A61F 9/00825; A61F 2009/00887; A61F 2009/0087; A61B 18/042; A61B 18/26; A61B 2018/005577; A61B 2018/00458; A61B 2018/2005; A61B 2018/266
USPC ....................................... 606/2; 6/2
See application file for complete search history.

(56) References Cited

U.S. PATENT DOCUMENTS 5,354,291 A * 10/1994 Bales .................. A61M 1/0045
                                                604/22
5,807,389 A *  9/1998 Gardetto ................ A61B 18/24
                                                606/15

(Continued)

FOREIGN PATENT DOCUMENTS

WO        9904737        2/1999

*Primary Examiner* — Gary Jackson
*Assistant Examiner* — Sebastian X Lukjan
(74) *Attorney, Agent, or Firm* — Workman Nydegger

(57) ABSTRACT

An applicator configured for cell treatment with pressure pulses has a hollow needle with a wall, which encloses a cavity and has a closed-off design at a closed-off end. A target is arranged or formed at the closed-off end on the inner side of the wall and a laser radiation emitter for emitting preferably pulsed laser radiation is arranged in the cavity of the hollow needle, at a distance from the target. The laser radiation emitter is arranged so that the emerging laser radiation impinges directly on the target through an interspace situated between the laser radiation emitter and the target. Under the formation of a plasma, at least one pressure pulse can be generated at the target by the target being impinged upon by laser radiation from the laser radiation emitter. The wall of the hollow needle has a lateral emergence opening for the emergence of the pressure pulse.

20 Claims, 5 Drawing Sheets

(51) Int. Cl.
*A61B 18/20* (2006.01)
*A61B 18/00* (2006.01)

(56) References Cited

U.S. PATENT DOCUMENTS

| | | | | |
|---|---|---|---|---|
| 5,957,914 A * | 9/1999 | Cook | ............... | A61B 18/26 |
| | | | | 606/10 |
| 6,346,108 B1 * | 2/2002 | Fischer | ............... | A61B 18/042 |
| | | | | 606/40 |
| 2004/0054357 A1 * | 3/2004 | O'Donnell | ............... | A61B 18/26 |
| | | | | 606/4 |
| 2004/0158236 A1 | 8/2004 | Thyzel | | |
| 2006/0229598 A1 * | 10/2006 | Shadduck | ............... | A61B 18/148 |
| | | | | 606/41 |
| 2007/0179485 A1 * | 8/2007 | Yeik | ............... | A61B 18/24 |
| | | | | 606/15 |
| 2010/0106054 A1 * | 4/2010 | Hangai | ............... | A61F 9/00763 |
| | | | | 600/566 |
| 2010/0160838 A1 * | 6/2010 | Krespi | ............... | A61B 18/26 |
| | | | | 601/15 |
| 2014/0121656 A1 * | 5/2014 | McKay | ............... | A61B 18/148 |
| | | | | 606/33 |

* cited by examiner

APPLICATOR AND DEVICE FOR CELL TREATMENT

CROSS-REFERENCE TO RELATED APPLICATIONS

This application claims the benefit of priority to German Patent Application No. 10 2012 106 017.7, filed Jul. 5, 2012, entitled "Applicator and Device for Cell Treatment," the entire content of which is incorporated herein by reference.

BACKGROUND OF THE INVENTION

1. Field of the Invention

The invention relates to an applicator and a device, respectively for cell treatment, in particular for epithelial cell removal or inactivation.

2. Background and Relevant Art

US 2002/0058890 A1 has disclosed a device for lithotripsy, which comprises an optical fiber and an absorber in the interior of a tubular housing. The optical fiber is connected to a laser at a first end and, at its other, second end, optically coupled to an inner side of the absorber facing the interior of the housing. When laser radiation from the laser impinges on the absorber on the inner side thereof facing the interior of the housing, the absorber generates a pressure wave, which is then, at the outer side of said absorber, transmitted through an end cap, encompassing the second end and the absorber, and emitted. Different shapes and/or propagation directions of the pressure wave can be achieved by different geometries of the end cap, for example in the style of lenses or cavities. The tubular housing does not have an emergence opening for the pressure wave; the absorber closes off the tubular housing at the free end thereof. As a result, a plasma possibly generated on the inner side of the absorber by the laser radiation remains in the interior of the housing.

WO 2004/071319 A1 has disclosed a surgical hollow needle for eye cataract treatment, with an optical fiber guided therein, wherein the optical fiber is coupled to a laser at its first end, situated outside of the hollow needle, and, at the second end thereof, the optical fiber is situated in the region of, and at a distance from, the tip of the hollow needle. In the region of the tip of the hollow needle, the latter has a target which is formed from a region of the wall of the hollow needle at the tip and at which a plasma is generated when irradiated by laser radiation of the laser from the fiber, as a result of which a pressure wave is created in turn. An opening, through which the pressure wave can reach the outside, is provided at the tip of the hollow needle. The lateral or side wall of the hollow needle is formed monolithically with the tip made of titanium (Ti) and embodied as continuous, smooth wall without an opening.

U.S. Pat. No. 5,324,282 has disclosed a surgical instrument in the form of a hollow needle for removing the lens of the eye by photolysis, which instrument has a tubular external wall with a longitudinal axis and a free end and also a laser fiber and a suction channel, which respectively extend longitudinally and in the interior of the needle up to the free end thereof. At the free end of the needle, a target made of titanium (Ti) is arranged at a distance from the free end of the laser fiber, wherein the laser light from the laser fiber impinges on the target. Furthermore, a tissue receiving opening, into which the suction channel opens, is provided at the free end of the needle, arranged obliquely and above the target and directly next to the latter. A suction pump is used to suction the tissue to be destroyed to the tissue receiving opening. When the tissue has now been suctioned to the tissue receiving opening, the target is bombarded with laser pulses from the laser fiber, wherein the laser pulses have sufficient energy to generate an optical breakdown in the target material and thereby generate a shockwave, which, at the tissue receiving opening, impinges on the tissue situated there and rips said tissue into small pieces which are then suctioned away through the suction channel. Furthermore, a longitudinally extending rinsing channel for guiding rinsing fluid through a laterally arranged emergence opening can additionally be provided in the needle.

U.S. Pat. No. 5,906,611 discloses a development of the instrument known from U.S. Pat. No. 5,324,282, in which the target has a step-shaped design and in which the steps are embodied with two step surfaces, of which one is aligned perpendicular to the needle axis and the other is aligned parallel to the needle axis, and the sequence of steps increases from an external side on the external wall of the needle toward the tissue receiving opening. As a result, when the target material is vaporized in each step zone of the target, the shockwave generated thereby is not blocked in the direction toward the tissue receiving opening by another part of the target. A neodymium-YAG laser can generate pulses with pulse repetition rates between 2 and 50 pulses per second and pulse energies between 2 and 15 mJ. The pulse duration can be set between 8 and 12 ns. The pulse repetition rate is preferably set between 2 and 6 pulses per second and the pulse energy is preferably set between 6 and 10 mJ. Between 200 and 800 pulses are used for a cataract operation.

A problem that occurs during surgical explantation or phacolysis of the natural eye lens and the subsequent implantation of an artificial intraocular lens is the subsequent growth and proliferation of the epithelial cells on the inner side of the lens capsular bag (PCO for posterior capsular bag opacification or secondary cataract or after cataract).

WO 2005/107665 A1 discloses a device for removing epithelial cells from the inner side of a lens capsular bag of a human or animal eye with means for generating pressure pulses in a liquid medium within the lens capsular bag, wherein the liquid medium adjoins or covers the epithelial cells to be removed, wherein the pressure pulses are selected or made in such a way that the epithelial cells are detached from the wall of the lens capsular bag by the impinging pressure pulses and, at the same time, no opening or other type of damage, in particular as a result of the pressure pulses, is created in the wall of the lens capsular bag when removing the epithelial cells. Use is preferably made of a laser handpiece in accordance with U.S. Pat. No. 5,324,282 or 5,906,611, but no negative pressure is created in the hollow needle in WO 2005/107665 A1 and no tissue is suctioned through the opening. Rather, the opening in the hollow needle in WO 2005/107665 A1 only serves for the emergence of the optically generated pressure pulses in the medium.

BRIEF SUMMARY OF THE INVENTION

It is now an object of the invention to specify an applicator and a device for cell treatment, in particular for epithelial cell removal or inactivation, preferably on the lens capsular bag of an eye, in particular for cell treatment in the case of PCO, by means of pressure pulses generated by laser radiation on a target, by means of which the risk of adversely affecting or damaging surrounding tissue that is not to be treated, in particular damaging the lens capsular bag itself, is reduced.

This object is achieved by the subject matter of the claims. Advantageous embodiments emerge from the dependent claims.

The applicator as per the claims is configured and intended for cell treatment, in particular for epithelial cell removal or inactivation, preferably on the human or animal eye, by means of pressure pulses, in particular shockwaves, and comprises a) a hollow needle with a wall, wherein the wall encloses a cavity and has a closed-off design at a closed-off end, b) wherein a target (or: bombardment material, bombardment target) is arranged or formed at the closed-off end on the inner side of the wall, c) wherein a laser radiation emitter for emitting preferably pulsed laser radiation is arranged in the cavity of the hollow needle, at a distance from the target and/or from the closed-off end, d) wherein a main emission direction of the laser radiation emitter is directed in the direction of the target or wherein, in other words, the laser radiation emitter is arranged in such a way that the emerging laser radiation impinges directly on the target through an interspace situated between the laser radiation emitter and the target, e) wherein, under the formation of a plasma, at least one pressure pulse, in particular by optical breakdown, can be or is generated at the target when the target is impinged upon or irradiated by laser radiation from the laser radiation emitter, f) wherein the wall of the hollow needle has a lateral (or: side) emergence opening for the pressure pulse to emerge from the cavity of the hollow needle and is completely closed off between the lateral emergence opening and the target or the closed-off end, g) wherein the lateral emergence opening is distanced from the target by a distance that is greater than the mean free path of the plasma in the cavity of the hollow needle and/or that is selected to be so long that substantially no plasma emerges from the cavity of the hollow needle through the lateral emergence opening.

The device according to the claims comprises at least one applicator according to the invention and a laser radiation source.

The invention is based on the idea of protecting the tissue which is not to be destroyed or treated, in particular the wall of the lens capsular bag, from being impinged upon by plasma which is created at the target as laser-induced plasma.

In the conventional application such as lens extraction, this laser-induced plasma is not damaging because it is more likely to contribute to the destruction of the tissue to be destroyed in any case. However, in the specific application, preferred according to the invention, of treating or avoiding (preventing) PCO, in which the epithelial cells are to be detached from the lens capsular bag or at least are to have their growth inhibited, the thin and self-supporting and hence sensitive tissue of the lens capsular bag, adjoining directly therebehind, must not be touched.

According to the invention, laser-induced plasma is already prevented from emerging from the emergence opening of the hollow needle provided for the pressure pulses. To this end, according to the invention, the hollow needle is closed off at the end with the target as a first measure, which means in particular that, in contrast to the prior art, there is precisely no opening in the corresponding axial end face of the hollow needle. According to a second measure, instead of an emergence opening at the end of the hollow needle, a lateral (or: side) emergence opening is now formed and arranged at a sufficiently large distance from the end of the hollow needle and the target arranged there such that the plasma can no longer emerge out of the lateral emergence opening, in contrast to the prior art, where the emergence opening is arranged at the tip of the hollow needle and directly adjoins the target. Although these measures according to the invention in principle also mean that an attenuation of the intensity of the pressure pulses emerging from this emergence opening is accepted, this is acceptable in applications such as e.g. capsule cleaning in which the intensity of the pressure pulses may in any case not be selected to be too high.

Within the scope of the present application, a pressure pulse is understood to mean a time-restricted pressure increase, in particular a pressure flow or pressure wave or shockwave, which propagates within the liquid medium toward the epithelial cells. Here, in addition to energy transport and impulse transport like in a wave, there can also be material transport like in the case of a current or a pressure beam.

The applicator and the device find a particularly advantageous application for removing (or: ablating, detaching, cutting, divulsing) or at least inactivating, i.e. in particular inhibiting (stunting the growth of), the epithelial cells from or on the inner wall of the lens capsular bag of an eye.

The applicator is preferably embodied as an in particular medical or surgical tool, which can be operated by hand and which can be introduced into the body of an organism for cell treatment of a predetermined tissue region. The in particular surgical hollow needle can be introduced into the organism, e.g. through the cornea in the eye lens, with its tip, e.g. in a percutaneous fashion. Depending on the penetration depth, the cell treatment can be carried out on dermal cells, subcutaneous cells or cells situated further inside.

In an advantageous embodiment, the laser radiation emitter comprises a laser radiation conductive fiber (abbreviated to: laser fiber or else optical fiber), the free end of which forms an emission surface for the laser radiation and the second end of which is or can be coupled directly or indirectly to a laser radiation source for coupling in the laser radiation thereof. The laser radiation conductive fiber in particular extends in the cavity of the hollow needle, preferably along the longitudinal axis thereof. The free end of the laser radiation conductive fiber, which forms the emission surface, is preferably arranged at a region of the wall of the hollow needle which is opposite to the lateral emergence opening and/or situated at a greater distance from the lateral emergence opening than the central longitudinal axis.

Furthermore, the lateral emergence opening, as seen along the longitudinal axis of the hollow needle and/or the main emission direction of the laser radiation emitter or the propagation direction of the pressure pulses, is preferably arranged between, on the one hand, the closed-off end of the hollow needle and/or the target and, on the other hand, the emission surface of the laser radiation emitter, in particular the free end of the laser radiation conductive fiber. Furthermore, the emergence opening in particular is formed and/or arranged symmetrically with respect to a symmetry plane containing the longitudinal axis of the hollow needle.

The main emission direction of the laser radiation is preferably parallel to the longitudinal axis of the hollow needle.

An active laser radiation emitter can also, alternatively or else additionally, be used in the hollow needle itself. Here, an active laser radiation emitter is to be understood to mean a laser radiation source which generates laser radiation directly, such as e.g. a laser diode or an array of laser diodes.

The target is designed and configured to generate an optical breakdown when laser radiation impinges on the target, which optical breakdown, under the formation of plasma, particularly in the medium, generates a pressure wave or shockwave.

Here, the target can be impinged upon in a pulsed fashion by laser radiation, i.e. by individual laser radiation pulses. Being impinged upon in a pulsed fashion should mean that an appropriate laser radiation source is operated in pulsed operation. For the application in the epithelial cell treatment, it is possible, for example, to use pulse rates of 1 to 10 pulses per second for laser radiation in wavelength range(s) of e.g. 532 to 1064 nm.

At least the target, in any case a section on which laser radiation impinges or is to impinge, is preferably made of metal, in particular titanium or a titanium alloy. In this case, it is possible, and may be advantageous, for the whole hollow needle, in particular the walls thereof, to be made of titanium. However, it is also possible to use other inert materials for the target or the wall of the hollow needle, such as e.g. zirconium (alloy) or instrument steel, e.g. 316 steel.

At least in the case of the intended use of the applicator, the hollow needle is, at least in an interspace or interior situated between the target and the lateral emergence opening, preferably filled with a liquid medium, e.g. irrigation liquid and/or salt solution such as BSS (Ringer's solution), for transmitting the pressure pulses wherein the plasma preferably forms in the liquid medium. The hollow needle is, preferably, situated entirely in the liquid medium and/or the liquid medium adjoins or covers the cells, in particular epithelial cells, to be treated in such a way that the pressure pulses can propagate or propagate to the cells through the liquid medium.

In a preferred embodiment, the wall of the hollow needle has a closure at the closed-off end of the hollow needle, on which closure the target is arranged or formed. The closure preferably has a convex, in particular dome-shaped, preferably substantially spherical or partly conical and partly spherical or only conical design, and/or is preferably arched or curved outwardly, particularly in the direction of a longitudinal axis of the hollow needle, as a result of which, preferably, an effect comparable to a lens or a focusing effect is obtained on the pressure pulse, in particular the shockwave, in the propagation direction from the target to the emergence opening. A radius of curvature of the curved closure is then, in general, dependent on the thickness or the diameter of the hollow needle and will generally be selected to be smaller than or equal to the diameter of the hollow needle.

Furthermore, the wall of the hollow needle is preferably formed substantially hollow cylindrically or as a cylindrical lateral wall, which, in particular, is formed about the longitudinal axis of the hollow needle as a cylinder axis, adjoining the closed-off end, in particular the closure, wherein the lateral emergence opening is then formed in this lateral wall.

According to a further particularly advantageous embodiment, the closed-off end is formed by a monolithic closure of the hollow needle. In particular, this should be understood to mean that the closure is formed monolithically, i.e. made of one piece and/or one material, with the adjoining region of the hollow needle. In this case, the closure is not a separate element which is detachably attached to the hollow needle. In this case, the closure can form an in particular curved section which can be considered part of the wall of the hollow needle.

Reference is merely made for the sake of completeness to the fact that the first end can also be closed off by a closure, e.g. a plug, which is detachably connected to the hollow needle. However, the aforementioned monolithic solution offers the advantage that there is no connection and there are no detachable parts, which could detach as a result of the generated shockwaves. The latter is of particular relevance since the hollow needle generally needs to be introduced into the organism.

A preferred spacing of the lateral emergence opening from the closed-off end of the hollow needle and/or the target is set in such a way that the distance is greater than an internal diameter and preferably also greater than an external diameter of the wall, preferably the lateral wall, of the hollow needle.

In a further particular embodiment, the opening is distanced from the target in the axial direction of the hollow needle and preferably arranged directly adjacent to the emission surface. Directly adjacent should, in particular, mean that a first edge of the opening, facing away from the closed-off end of the hollow needle, approximately touches a plane, perpendicular to the axial direction, through the emission surface. The perpendicular plane through the emission surface can also be referred to as emission plane.

In an advantageous embodiment, the emergence opening has a substantially circular design with a diameter about a central axis preferably aligned perpendicular to the longitudinal axis. The diameter is smaller than the external diameter, but preferably greater than the internal diameter, of the hollow needle, in particular of the lateral wall. Such an emergence opening is preferably produced by chip-removing drilling through the wall, in particular the lateral wall, from the outside by means of a drill with a drilling direction aligned substantially perpendicular to the longitudinal axis.

In a particularly advantageous embodiment, the emergence opening is formed as an elongate hole, which extends parallel to the longitudinal axis (A) with a longitudinal direction or the (larger) longitudinal dimension and which, in particular, has an oval shape or else a stadium shape with two semicircular edge segments which are connected by edge segments extending in a straight line parallel to the longitudinal axis. A transverse dimension of the emergence opening, which is smaller than the longitudinal dimension, now is preferably smaller than the external diameter, but preferably greater than the internal diameter, of the hollow needle, in particular of the lateral wall.

In particular, a pan-like volume for a plasma created in the case of optical breakdown can emerge between the first end, i.e. the target, and the second edge of the opening. The mean free path of the plasma is shorter than the axial extent of the pan-like volume, and so it is possible to prevent the plasma from emerging from the interior of the hollow needle.

A further embodiment of the applicator provides for the diameter of the hollow needle to reduce from the axially open end to the closed-off end, preferably in a step-like fashion. A transition or transition region between two segments with different diameters is preferably formed as a cone, i.e. as a frustum. In the case of appropriate diameters of the two segments, the frustum forms an intermediate segment which conically tapers toward the closed-off end.

According to one embodiment of the applicator, the emission surface, to the extent that it is applicable the diameter of the optical fiber, in particular the whole optical fiber, is preferably smaller, preferably significantly smaller, than the smallest internal diameter of the hollow needle. For the optical fiber, an interspace emerges between the inner wall of the hollow needle and the optical fiber for this configuration. By way of example, this interspace can be used as a communication channel.

In particular, by means of the aforementioned embodiments, it is possible to influence, in an advantageous fashion, the generation of the plasma, and hence a generation of a shockwave, and also the propagation of the shockwave such that a comparatively advantageous, in particular improved, lithotriptic effect emerges outside of the hollow needle, in particular by the propagation of the shockwave through the opening.

According to claim 11, provision is made for a device for in vivo cell lithotripsy. The device comprises an applicator in accordance with at least one of the above-described embodiments or configurations. In respect of advantages and advantageous effects, reference is made in particular to the explanations above.

The device can comprise a laser radiation source situated outside of the hollow needle, which laser radiation source is or can be optically coupled to the optical fiber for coupling in laser radiation. Furthermore, the device can comprise an electronic control for operation, more particularly for pulsed operation, of the laser radiation source.

BRIEF DESCRIPTION OF THE DRAWINGS

In the following text, exemplary embodiments of the invention are described in more detail with reference to the attached drawings in which.

Mutually corresponding parts and variables are denoted by the same reference signs in FIGS. 1 to 7.

DETAILED DESCRIPTION OF THE PREFERRED EMBODIMENTS

Figure 1:
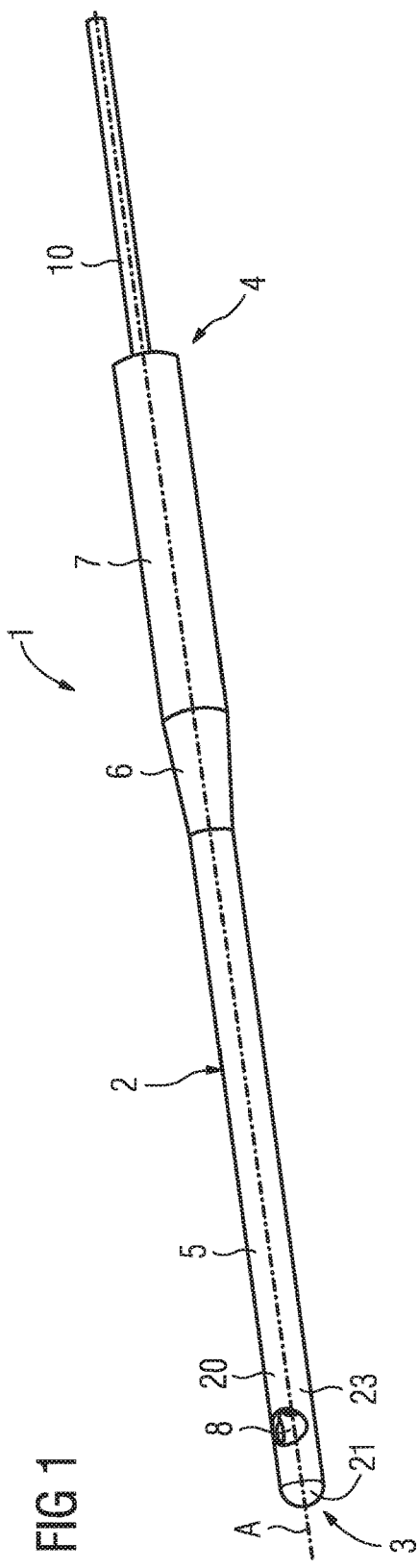
FIG. 1 shows a perspective view of an applicator for cell treatment, with a round lateral emergence opening.
Figure 2:
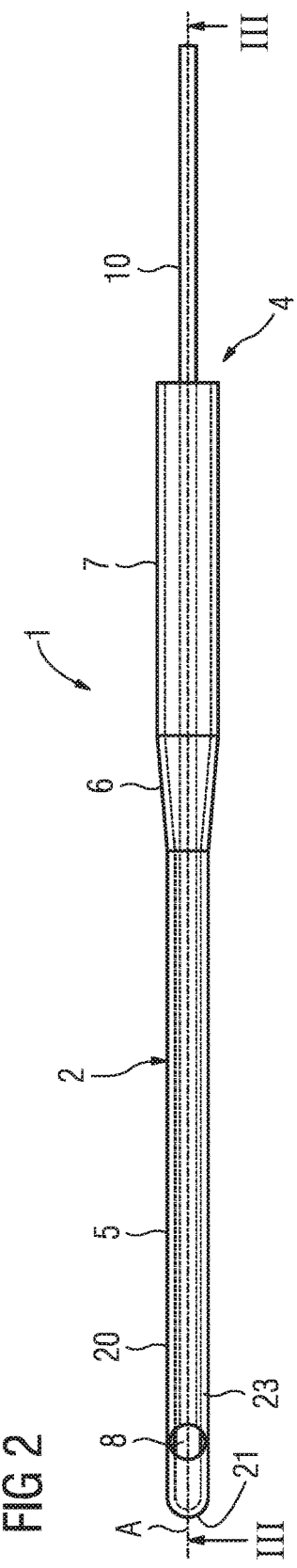
FIG. 2 shows a plan view of the applicator in accordance with FIG. 1.
Figure 3:
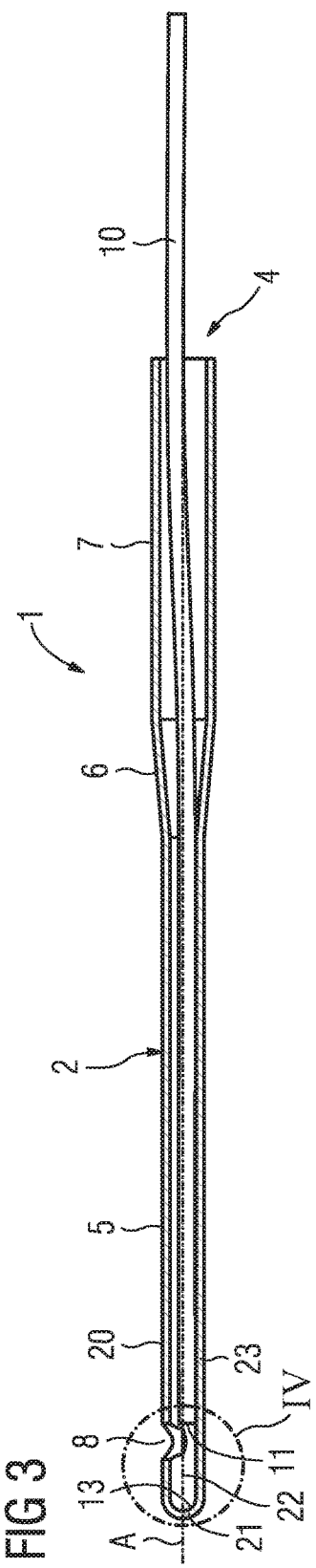
FIG. 3 shows an axial section through the applicator in accordance with line III-III in FIG. 2.

FIGS. 1 to 7 show exemplary embodiments of applicators 1 for cell treatment, in general taking place in vivo, in particular destruction or inactivation of epithelial cells on the lens capsular bag of an eye, e.g. for treating or preventing PCO. In principle, the applicator 1 is not restricted to the treatment of epithelial cells, but it is particularly suitable for this.

The applicator 1 comprises a hollow needle 2, which has a closed-off design at a first, free end 3 and has an opposing second end 4.

In the axial direction of a longitudinal axis A, proceeding from the free first end 3 to the second end 4, the hollow needle 2 comprises, connected in series and preferably with an integral design, a first segment 5 with the first end 3, an intermediate segment 6 and a second segment 7 with the second end 4. The first segment 5 has a smaller external diameter D than the second segment 7, as a result of which there is a configuration where the external diameter, and preferably also the internal diameter, reduces toward the first end 3. In order to bridge the different external diameters of the first segment 5 and the second segment 7, the intermediate segment 6 is, in FIGS. 1 to 3, designed with a conical taper toward the first end 3, while, in FIG. 5, it is practically designed in the form of a step or in a step-like manner.

The wall 20 of the hollow needle 2 can have an external diameter D of approximately 0.8 mm in the first segment 5 while having a wall strength of approximately 0.1 mm and an external diameter of approximately 1.2 mm in the second segment 7 while having approximately the same wall strength. In the case of the given external diameters, the intermediate segment 6 can have an aperture angle of approximately 10 degrees, as seen in the direction from the first end 3 to the second end 4.

The whole hollow needle 2 can have a length of approximately 22.5 mm, wherein the second segment can, for example, have a length of 7 mm.

The wall 20 of the hollow needle 2 encloses a cavity (or: channel) 22 in the interior of the hollow needle 2 and has, at the free first end 3, a dome-shaped closure 21, in which, on the inner side facing the cavity 22, a target (or: bombardment material) 13 is arranged or formed. The inner wall of the closure 21 is denoted by 24. Adjoining the closure 21 and the free first end 3, the wall 20 of the hollow needle 2 continues in the first segment 5 as a cylindrical lateral wall 23, which extends along the longitudinal axis A of the hollow needle 2 (as cylinder axis). The lateral wall 23 has an axially unchanging external diameter D and an axially unchanging internal diameter y, which forms the diameter of the region of the cavity 22 surrounded by the lateral wall 23.

The target 13 is preferably formed by a portion of the closure 21 or else as wall section of the wall 20 and the closure 21 consists of the target or bombardment material of the target 13. Furthermore, the closure 21 is preferably formed integrally or monolithically with the remaining regions or formed from the same material as the lateral wall 23. The material of the target 13 and, optionally, of the closure 21 and the lateral wall 23 is preferably titanium or a titanium alloy.

During the in vivo cell treatment, the hollow needle 2 is generally situated in a liquid medium M, in particular an irrigation fluid, and is filled with the latter.

In the first segment 5 of the hollow needle 2, a laser radiation conductive fiber 10 (also abbreviated as fiber 10 in the following text), which extends parallel to the longitudinal axis A, lies against the inner side of the lateral wall 23 in the cavity 22. In the cavity 22 in the intermediate segment 6 and second segment 7, the fiber 10 is not attached to the wall 20 of the hollow needle 2, and emerges substantially axially from the cavity 22 of the hollow needle 2 at the second end 4 of the hollow needle 2, which is open. As a result of the loose arrangement of the fiber 10 in the intermediate segment 6 and the second segment 7 without being attached to the wall 20, the fiber 10 can extend freely with curvature or with a bend and can, as a result, be flexibly coupled without relatively large mechanical tension to a coupling device (not illustrated), in particular an optical plug-in connection, for coupling to a laser radiation source (not illustrated) for emitting laser radiation L.

Together with the laser radiation source and, optionally, the coupling device, the applicator 1 forms a device for cell treatment, in particular epithelial cell treatment.

Figure 4:
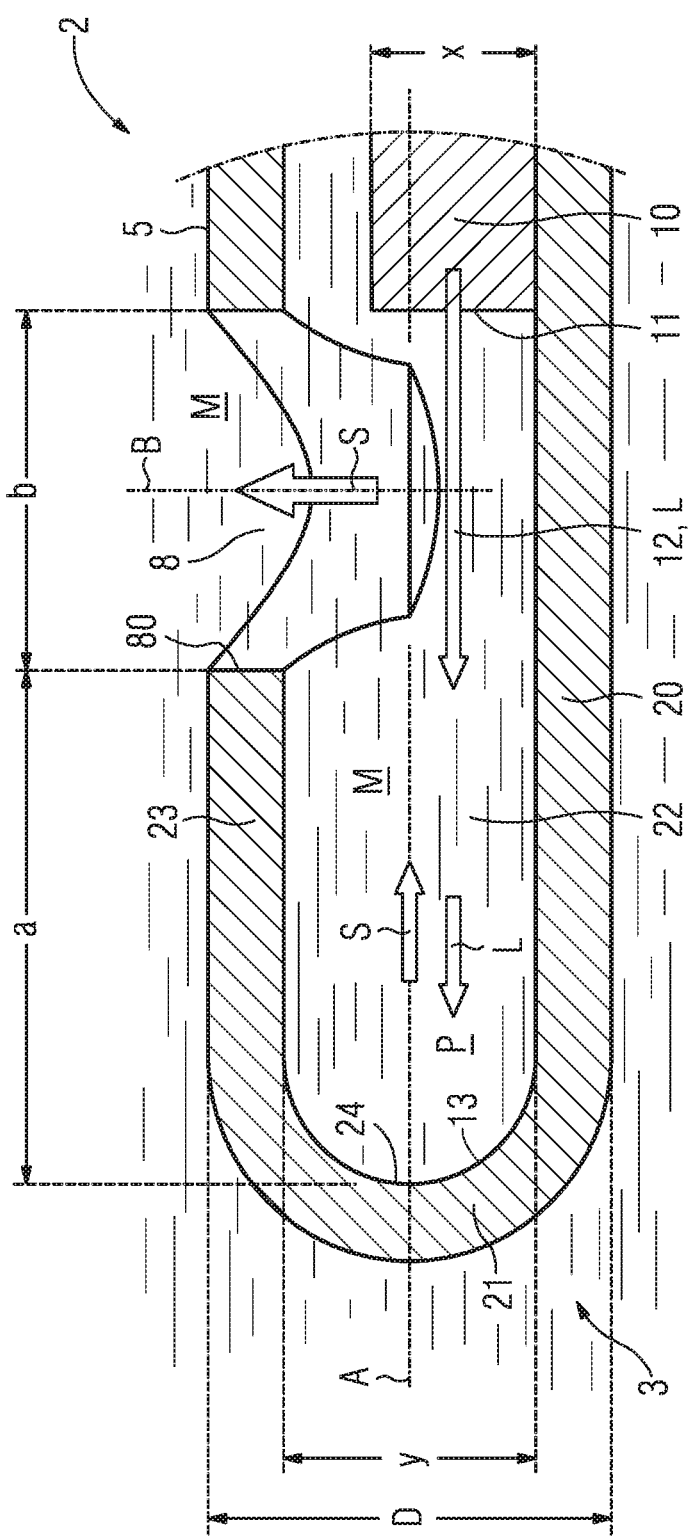
FIG. 4 shows an axial section of a magnified detail, denoted by IV in FIG. 3, of the front region of the applicator.

The laser radiation conductive fiber 10 transmits the coupled-in laser radiation L as far as a free end of the fiber, at which the laser radiation L reemerges from the fiber 10 and the end face of which end therefore forms an emission surface 11 for the laser radiation L. In FIG. 4, the emission surface 11 lies in a plane perpendicular to the longitudinal axis A. A main emission direction 12 of the laser radiation L is directed at the target 13 on the closure 21 in the direction of the first free end 3. In the present case, the main emission direction 12 runs parallel to the longitudinal axis A and hence orthogonal to the emission surface 11. It follows that the laser radiation L emerging from the fiber 10 into the cavity 22 is transmitted, through the interspace in the cavity 22 between the emission surface 11 and the target 13, to the target 13 on the closure 21 in the main emission direction 12, generally through the liquid medium M which is situated in the cavity 22 and also outside of the hollow needle 2, and impinges on the target material.

As a result of this impingement or irradiation of the target 13 with laser radiation L, more precisely with laser radiation pulses, with a correspondingly high energy, in particular 4 to 12 mJ at e.g. a wavelength of 1064 nm, or power, a shockwave or pressure wave S as pressure pulse, in this case in the liquid medium M, can be generated on the target 13 by an optical breakdown or laser radiation breakdown in the target material created in the process, and a plasma P being generated accompanying this, and can be transmitted further. The propagation directions of the shockwave S are illustrated by two broad arrows.

The hollow needle 2 now has a lateral (or: side) emergence opening 8, which passes through the wall 20 and preferably points outward, radially or perpendicularly to the longitudinal axis A, for emergence or passage of the shockwave or the pressure pulse S from the cavity 22 of the hollow needle 2 to the outside. This lateral emergence opening 8 is generated or arranged in the lateral wall 23 of the hollow needle 2 in the region of the first segment 5. The emergence opening 8 is formed about a central axis B, which is preferably aligned perpendicular to the longitudinal axis A and extends radially with respect to the latter.

The emergence opening 8 preferably is symmetrical or lies symmetrically with respect to a symmetry plane containing the longitudinal axis A of the hollow needle 2 and preferably spanned by the longitudinal axis A and the central axis B.

The edge of the emergence opening 8 formed by the wall 20 or 23 is denoted by 80.

In FIGS. 1 to 4, the emergence opening 8 is formed to be approximately circular in the plan view or in the cross section, with a diameter (or in general: a clear width) b, which is less than the external diameter D but in general greater than the internal diameter y of the hollow needle 2 or the lateral wall 23, i.e. y< b< D.

Such a round emergence opening 8 can be produced by chip-removing drilling through the lateral wall 23 from the outside by means of a drill with a drilling direction aligned substantially perpendicular to the longitudinal axis A.

The edge 80 of the emergence opening 8 emerges from the geometric cut from a cylinder with the diameter b along the central axis B through the cylinder with the diameter D along the longitudinal axis A of the lateral wall 23 and therefore has a hood-shaped design, as illustrated.

Figure 5:
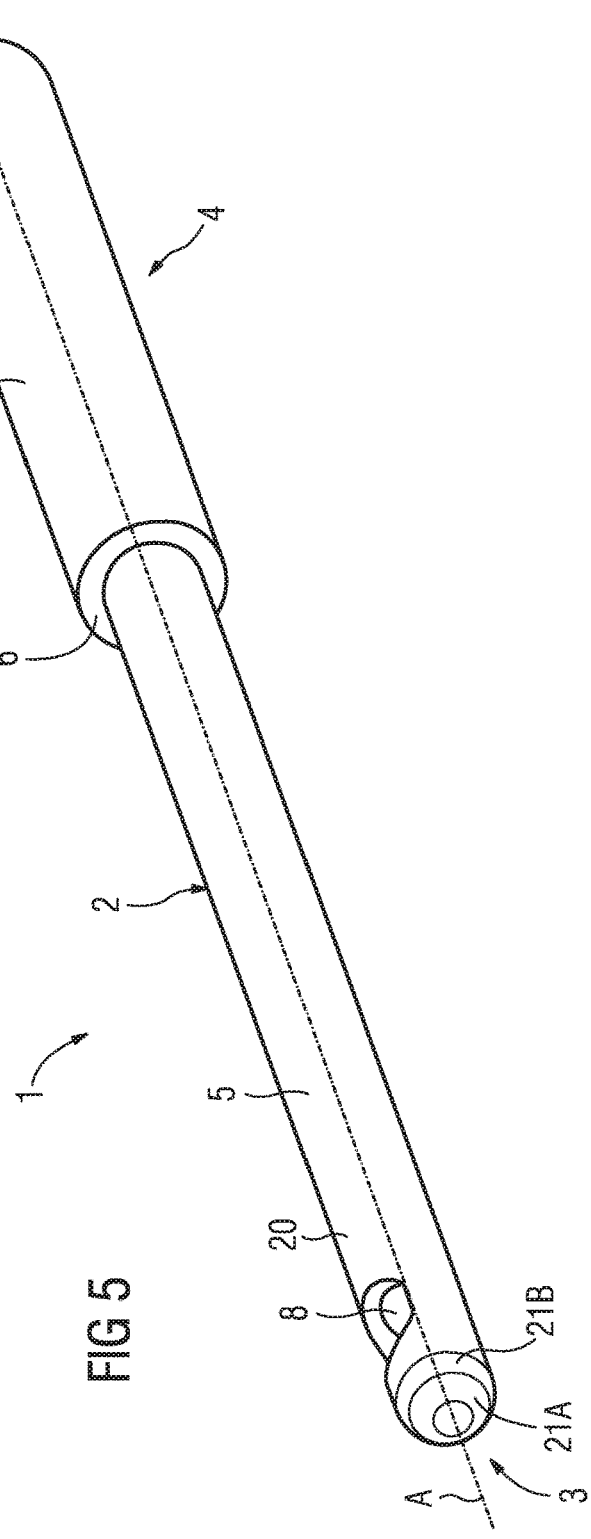
FIG. 5 shows a perspective view of an applicator for cell treatment, with an elongate lateral emergence opening.
Figure 6:
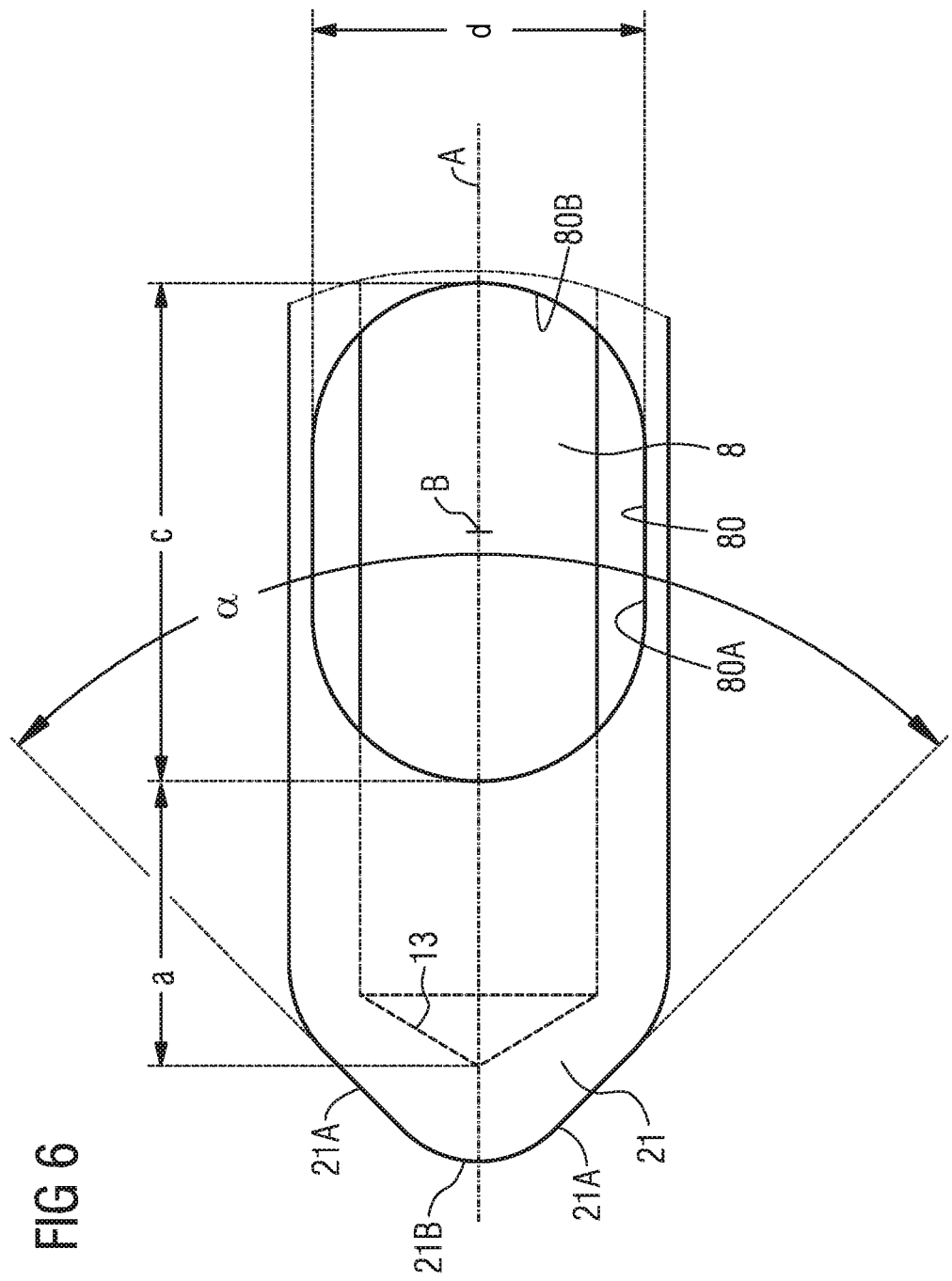
FIG. 6 shows a plan view of the front region of the applicator in accordance with FIG. 5.
Figure 7:
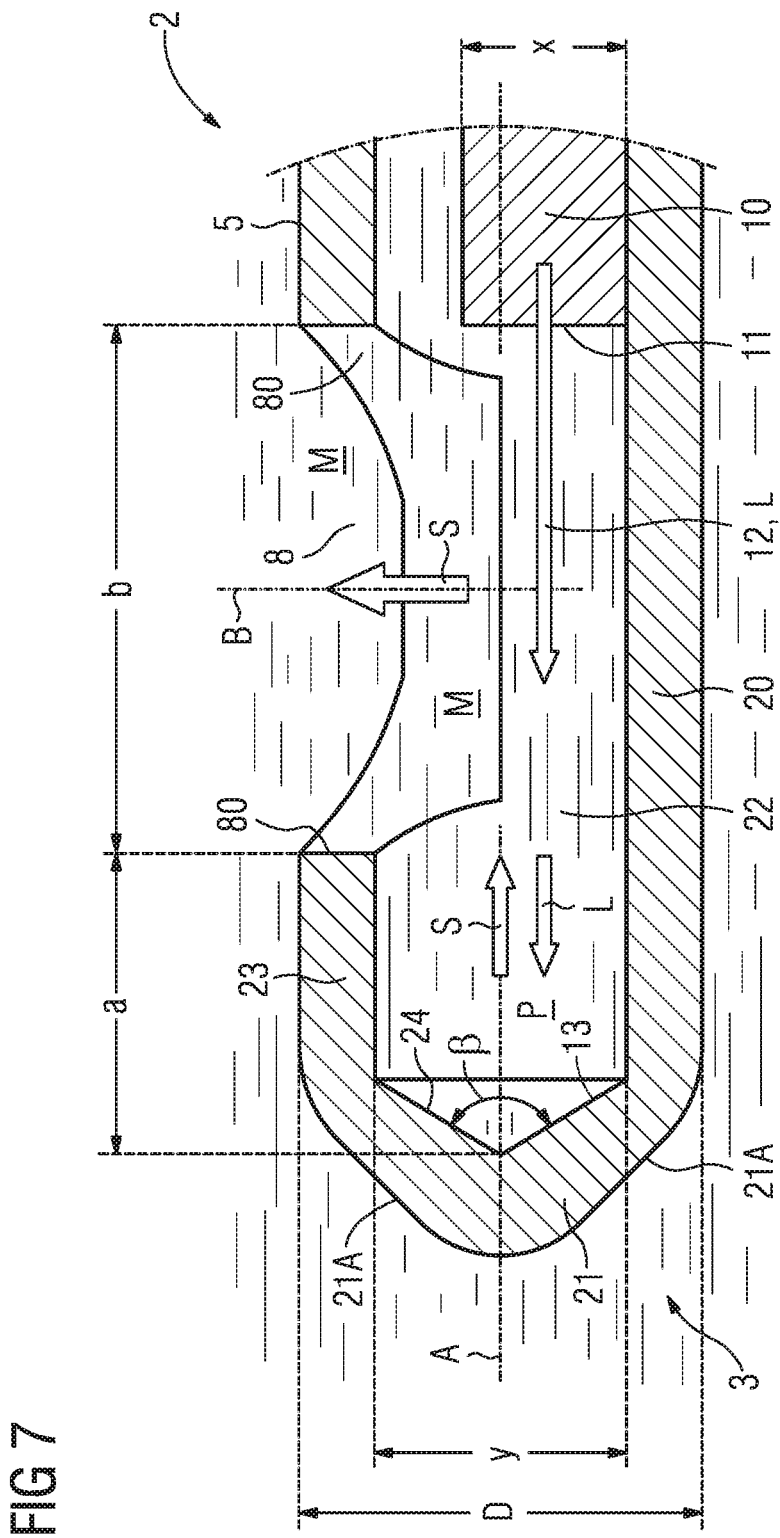
FIG. 7 shows an axial section of the front region of the applicator in accordance with FIGS. 5 and 6.

By contrast, in FIGS. 5 to 7, the side emergence opening 8 is embodied as elongate hole, which extends parallel to the longitudinal axis A with a longitudinal direction. The longitudinal dimension of the emergence opening 8 parallel to the longitudinal axis A is denoted by c and the transverse dimension of the emergence opening 8 perpendicular to the longitudinal axis A and to the longitudinal dimension c is denoted by d. In this embodiment, the edge 80 of the emergence opening 8 is formed by two semicircular edge segments 80B which are connected by edge segments 80A extending in a straight line parallel to the longitudinal axis A such that this results in a stadium-like shape.

Reference is made to the fact that the dimensions such as the clear width b or the longitudinal dimension c and the transverse dimension d of the emergence opening 8 are modified or adapted depending on the generated shockwaves or the shockwaves to be generated.

The closure 21 has a convex, more particularly dome-shaped, design. In accordance with FIGS. 1 to 4, the closure 21 is preferably arched outward or curved, in particular in the direction of the longitudinal axis A, which closure is preferably substantially spherically, in particular with a center point on the longitudinal axis A. Thus, the external wall of the closure 21 forms a spherical blunt tip of the hollow needle 2. As is possible to identify from FIG. 4, the inner wall 24 of the closure 21 with the target 13 also has a spherical design, preferably with a center point on the longitudinal axis A, preferably the same center point as the external wall.

In accordance with FIGS. 5 to 7, the closure 21 is, on its external side, assembled from an external partial wall region (or: external cone) 21A, formed conically about the longitudinal axis A, with the external cone angle α, which is selected between 80° and 100°, in particular at approximately 90°, and a central spherically curved inner partial wall region 21B, which forms a blunt tip of the hollow needle 2. The partial wall regions 21A and 21B merge smoothly (in a continuously differentiable fashion) into one another. An inner cone shape with a tip and an internal cone angle β, which is selected between 100° and 160°, in particular at approximately 120°, is realized on the inner side or inner wall 24 of the closure 21, which inner cone shape can, in particular, be created by a drill tip when drilling the cavity 22.

As a result of the curvature or at least the convexity, there is a focusing effect, comparable to that of a lens, on the pressure pulse, more particularly the shockwave S, in the propagation direction from the target 13 to the lateral emergence opening 8 in both shapes of the closure 21. A blunt free end 3 of the hollow needle 2 is also created in both cases, which reduces the risk of injury to tissue when moving the hollow needle 2.

The pressure pulse or the shockwave S initially propagates through the cavity 22 from the target 13 and then, through the lateral emergence opening 8, to the outside into the medium M which is also situated outside of the hollow needle 2 and said pressure pulse or shockwave can be used outside of the hollow needle 2 in tissue adjacent to the emergence opening 8 for cell treatment, in particular destruction, inactivation and/or removal of appropriate cells, in particular epithelial cells on the lens capsular bag of the eye.

With its edge 80, the lateral emergence opening 8 is now distanced from the first end 3 or the inner side of the closure 21 or the target 13 by an axial distance a in the axial direction toward the longitudinal axis A or the center axis B of said lateral emergence opening is distanced by a distance a+b/2.

The distance a between the first end 3 and the opening 8 is preferably selected to be longer than the mean free path of the plasma P which is created at the target 13. As a result of this, it is advantageously possible, at least to a large extent, to prevent the plasma P from emerging from the emergence opening 8, which can have a positive effect on the cell-treating effect of the applicator 1 since the plasma P cannot directly touch the surrounding cell tissue which is not to be treated, nor can it directly touch the cell tissue to be treated either. Hence, only the shockwave S in the surrounding medium M impinge on the cell tissue to be treated.

The distance a is selected to be greater than the internal diameter y of the cavity 22 of the hollow needle 2, i.e. a>y, and preferably also greater than the external diameter D of the hollow needle 2, i.e. a>D, and, furthermore, also to be greater than the diameter or the longitudinal dimension b of the emergence opening 8, i.e. a>b. Absolute values for the distance a preferably lie at at least 0.7 mm, preferably between 0.8 mm and 1.9 mm. Furthermore, the distance a is generally selected to be greater if the energy of the laser radiation pulse is higher and/or if the pulse is shorter, and it is selected to be smaller if the energy is smaller or the pulse is longer.

As can be seen from FIG. 4 in particular, the external dimension of the emission surface 11, and, in the present case, also the diameter x of the fiber 10, is smaller than the internal diameter y of the first segment 5. As a result of the present geometries, the diameter x of the fiber 10 is also smaller than the internal diameter of the intermediate segment 6 and of the second segment 7. A suitable fiber diameter x is approximately 350 μm.

As shown in FIG. 4, the emission surface 11, and accompanying this at least a terminating section of the fiber 10, is placed on the inner side of the wall 20 and the lateral wall 23 thereof, lying opposite to the emergence opening 8, and/or arranged at an axial distance from the target 13 or the inner side of the closure 21, which axial distance is at least a+b, preferably equals a+b, i.e. terminates flush with the edge of the emergence opening 8 facing away from the target. This prevents laser radiation L from being able to emerge directly from the opening 8.

Correspondingly, the axial distance of the emission surface 11 from the target 13 or the inner wall 24 equals or is greater than a+c in FIGS. 6 and 7.

An approximately pan or bowl-shaped region emerges within the hollow needle 2 between the first end 3 and the emergence opening 8, particularly with the specified geometric conditions. This bowl-shaped region is advantageous inasmuch as the plasma remains at least partly trapped therein, i.e. an emergence from the hollow needle is substantially prevented. In the case of an appropriate radiation power of the laser radiation source, a plasma is generated, the free path of which is shorter than the axial length of the bowl-shaped region, and what is achieved is that the plasma remains in the hollow needle 2 to a substantial degree.

In order to prevent damage to the fiber 10, the edges of the hollow needle 2, i.e. of the second segment 7, are formed in a burr-free fashion in the region of the second end 4.

Since optical fibers require comparatively little installation space, hollow needles with a comparatively thin cross section can be used for the applicator. However, it should be mentioned that the use of laser radiation sources within the hollow needle is also possible, provided that enough installation space is available.

In the following text, a cataract operation with post cataract prevention is described as a particularly advantageous application of the applicator and the device. A cataract operation generally comprises the following method steps:

First of all, a surgical instrument, for example a cannula, is used to open the front capsular bag, wherein an opening with dimensions of, in general, 4.5 mm to 5.5 mm is created (capsulorrhexis). Then, incisions are created, generally at opposite sides, in the cornea, in particular on the limbus, on the one hand for a photolytic laser handpiece and, on the other hand, for an irrigation handpiece. As a result of introducing a rinsing liquid, e.g. BSS, the eye lens is detached from the capsular bag and mobilized as a result thereof (hydrodissection). Rinsing fluid, generally likewise BSS, is now rinsed into the capsular bag by means of the irrigation instrument and, as a result of the pressure of the rinsing fluid built up thereby, the rear wall of the capsular bag is, in particular, prevented from coming too close to the laser handpiece, and the capsular bag is rinsed at the same time.

The eye lens is successively photolytically decomposed by the pressure pulses or shockwaves generated by laser pulses and suctioned away, preferably by means of the applicator according to the invention or, optionally, also by means of a different applicator, which can, for example, be a laser handpiece by A.R.C. Laser GmbH or can have a design in accordance with U.S. Pat. No. 5,324,282 or 5,906,611, as mentioned at the outset. Here, the eye lens, in particular the nucleus thereof processed at the end, can be moved by means of the irrigation tool and optimized in terms of its position relative to the applicator. The tissue of the lens is destroyed piece by piece by means of a multiplicity of laser pulses and the shockwaves triggered thereby and the individual tissue parts can be suctioned away. Following the complete removal of the natural eye lens, an artificial eye lens is now subsequently inserted into the capsular bag. The surgeon operates with both instruments using a bi-manual technique.

In accordance with the invention, the capsular bag inner side is now rid of epithelial cells by means of the applicator or a device according to the invention in order to avoid PCO, either before introducing the artificial lens or, preferably, after inserting the artificial lens since the artificial lens then seals the opening in the front capsular bag generated by capsulorrhexis.

The wall of the lens capsular bag is now relatively thin and sensitive. As a result, the lens capsular bag is not able to maintain its shape after removing the natural eye lens, and so the capsular bag can nevertheless at least in part fall in on itself, even if rinsing fluid is introduced, and thus there is a risk of damage by the applicator.

It has already been shown that the generated, comparatively strong shockwaves or pressure pulses are, nevertheless, generally harmless to the capsular bag wall if the capsular bag wall is sufficiently relaxed and can give way by deformation. Thus, a tense or, as it were, rigid capsular bag wall should be avoided when the shockwave for removing or divulsing the epithelial cells impinge thereon. It is for this reason that no suction function or only a low suction function is used during the epithelial cell removal and no negative pressure or only a small negative pressure is generated by means of a pump or the like so that the shockwave is not incident on the capsular bag wall in the strongly suctioned state or the capsular bag wall is not already suctioned in as a result of the negative pressure during suctioning and a tear or opening is created.

In general, the pulse repetition rate for the laser radiation pulses, i.e. the number of laser radiation pulses applied per unit time, for example per second, is also kept so low that the capsular bag wall can return or oscillate back to a relaxed state after a laser radiation pulse and a shockwave generated thereby before the next laser radiation pulse and the associated shockwave, and, as a result, is specifically not in the deformed position, and hence under (maximum) tension, when the next laser radiation pulse impinges, in which position the capsular bag is liable to rip. The capsular bag should therefore so to speak be able to oscillate with the repeated pressure pulses.

According to the invention, it was surprisingly discovered that the plasma, which is created during the optical generation of the pressure pulses by means of the laser radiation and which emerges from the applicator in known applicators, can also impinge on the capsular bag wall through the liquid medium and can surprisingly also lead to cellular damage there in the tissue adjacent to the epithelial cells.

According to the invention, such an emergence of plasma is therefore substantially prevented by the above-described special design of the hollow needle of the applicator. However, the strength of the pressure pulses at the same time remains sufficient for ablating the epithelial cells.

Hence, what is achieved by this preferred application with the aid of the applicator and the associated device is a sparing and effective removal or at least inactivation of epithelial cells on the lens capsular bag of an eye, in particular within the scope of preventing a secondary cataract or PCO.

The pulse repetition rate of the pressure pulses of the device is, preferably already on the operating unit, restricted to in particular at most 10 Hz, i.e. 10 pulses per second, more particularly at most 4 Hz, by an appropriate actuation of the laser radiation pulses. However, in principle, higher frequencies are also possible. No restriction is required downward and it is possible to set pulse repetition rates down to nearly 0 Hz. The pressure pulses can be shockwaves or pressure waves or else be pressure currents or pressure beams connected with material transport.

The frequency spectrum of the pressure wave before forming the shockwave as a result of nonlinear effects can range from the region of a few Hz up to the region of 100 kHz, whereby, in addition to sound oscillation in the audible range, ultrasonic waves or oscillations are also possible.

LIST OF REFERENCE SIGNS

1 Applicator
2 Hollow needle
3 First end
4 Second end
5 First segment
6 Intermediate segment
7 Second segment
8 Emergence opening
10 Fiber
11 Emission surface
12 Main emission direction
13 Target
20 Wall
21 Closure
21A Partial wall
21B Partial wall
22 Cavity
23 Lateral wall
24 Inner wall
75 Transition
80 Edge
80A Edge segment
80B Edge segment
A Longitudinal axis
B Central axis
a Distance
b Diameter
c Longitudinal dimension
d Transverse dimension
D External diameter
x Fiber diameter
y Internal diameter
L Laser radiation
M Liquid medium
P Plasma
S Pressure pulse, in particular shockwave
α External cone angle
β Internal cone angle

I claim:

1. An applicator, configured and intended for cell treatment, for epithelial cell removal or inactivation by means of pressure pulses and comprising:
   a) a hollow needle with a wall, which encloses a cavity and has a closed-off design at a closed-off end, wherein the hollow needle is situated in a liquid medium;
   wherein:
   b) a target area comprising a metal is arranged within the closed-off end on the inner side of the wall of the hollow needle;
   c) a laser radiation emitter for emitting pulsed laser radiation (L) is arranged in the cavity of the hollow needle, at a distance from the target area within the closed-off end;
   d) the laser radiation emitter is arranged in such a way that the emerging laser radiation (L) impinges directly on the target area within the closed-off end through an interspace situated between the laser radiation emitter and the target area, the target area being kept from contact with tissue by the closed-off end;
   e) under the formation of a plasma (P), at least one pressure pulse (S) is generated at the target area by the target area being impinged upon by laser radiation (L) from the laser radiation emitter;
   f) the wall of the hollow needle has a lateral emergence opening for the pressure pulse (S) to emerge from the cavity of the hollow needle and is completely closed off between the lateral emergence opening and the target area within the closed-off end; and
   g) the wall of the hollow needle has, at the closed-off end of the hollow needle, a closure on which the target area is arranged, the closure being formed to be convex and dome-shaped on the outside and the inner wall,
   h) the wall of the hollow needle, following on from the closure, forms a cylindrical liner wall around a longitudinal axis (A) of the hollow needle as a cylinder axis,
   i) the lateral emergence opening is formed in the cylindrical liner wall, and
   j) the lateral emergence opening is spaced apart from the closure of the hollow needle and the target area by an axial distance (a) to the target area which is larger than an outer diameter (D) of the cylindrical liner wall of the hollow needle.

2. The applicator as claimed in claim 1, wherein:
   the hollow needle is, at least in an interspace situated between the target area and the lateral emergence opening, filled with the liquid medium for transmitting the pressure pulses (S);
   the plasma (P) forms in the liquid medium (M); and
   the liquid medium adjoins or covers the cells to be treated in such a way that the pressure pulses (S) reach the cells through the liquid medium without direct contact with the target area inside the closed-off end.

3. The applicator as claimed in claim 1, wherein:
the wall has a closure at the closed-off end of the hollow needle, on which closure the target area is arranged or formed; and
the closure, has a convex, dome-shaped design on the outer side and the inner side or inner wall.

4. The applicator as claimed in claim 1, wherein:
the wall of the hollow needle forms a cylindrical lateral wall about the longitudinal axis (A) of the hollow needle as a cylinder axis, adjoining the closed-off end; and
the lateral emergence opening is formed in the lateral wall.

5. The applicator as claimed in claim 1, wherein the lateral emergence opening is distanced from the closed-off end of the hollow needle and the target area by a distance (a) that is greater than an external diameter (D), of the lateral wall, of the hollow needle and that is between 0.8 mm and 1.9 mm.

6. The applicator as claimed in claim 1, wherein:
the laser radiation emitter comprises a laser radiation conductive fiber, the free end of which forms an emission surface for the laser radiation (L) and a second end of which is coupled to a laser radiation source for coupling laser radiation from the laser radiation source into the laser radiation conductive fiber.

7. The applicator as claimed in claim 1, wherein the emergence opening is symmetrical with respect to a symmetry plane containing the longitudinal axis of the hollow needle and also a central axis (B) which is aligned perpendicular to the longitudinal axis (A) and passes through the center of the emergence opening.

8. The applicator as claimed in claim 1, wherein:
the emergence opening has a circular design with a diameter (b) about a central axis (B) aligned perpendicular to the longitudinal axis (A); and
the diameter (b) is smaller than the external diameter (D), but greater than the internal diameter (y), of the hollow needle of the lateral wall.

9. The applicator as claimed in claim 1, wherein:
the emergence opening is formed as an elongate hole, which extends parallel to the longitudinal axis (A) with a longitudinal direction or the longitudinal dimension (c) and which has an oval shape or else a stadium shape with two semicircular edge segments which are connected by edge segments extending in a straight line parallel to the longitudinal axis (A); and
a transverse dimension (d) of the emergence opening, which is smaller than the longitudinal dimension (c), is smaller than the external diameter (D), but greater than the internal diameter (y), of the hollow needle of the lateral wall.

10. The applicator as claimed in claim 1, wherein:
the diameter of the hollow needle reduces from a second opposite end to the closed-off first end;
an axial first segment of the hollow needle, containing the closed-off first end, has a first external diameter and an axial second segment of the hollow needle, containing the second opposite end, has a greater external diameter than the first external diameter;
a transition between the axial first and second segments of the hollow needle which respectively have a constant but mutually different diameter is formed by an intermediate segment which conically tapers towards the closed-off end or else forms a step; and
the laser radiation conductive fiber is attached to the wall in the axial first segment of the hollow needle and not attached to the wall in the axial second segment of the hollow needle and in the intermediate segment.

11. A device for application or configured and intended for cell treatment, for epithelial cell removal or inactivation, by means of pressure pulses, called shockwaves (S), comprising:
an applicator as claimed in claim 1, and
at least one laser radiation source for generating laser radiation (L).

12. The device as claimed in claim 11, wherein:
the laser radiation is pulsed with a pulse duration between 5 ns and 20 ns, and a pulse energy between 1 and 20 mJ;
each laser pulse generates at least one pressure pulse;
the hollow needle is at least predominantly filled with the liquid medium; and
the hollow needle is situated in the liquid medium and the liquid medium adjoins or covers the cells to be treated in such a way that the pressure pulses (S) reach the cells through the liquid medium.

13. The applicator as claimed in claim 1, wherein:
the wall has a closure at the closed-off end of the hollow needle, on which closure the target area is arranged or formed; and
the closure is at least partly spherical, arched, curved or at least has a conical shape in the direction of the longitudinal axis (A) of the hollow needle.

14. The applicator as claimed in claim 1, wherein:
the laser radiation conductive fiber extends in the cavity of the hollow needle along the longitudinal axis (A) thereof.

15. The applicator as claimed in claim 1, wherein:
the free end of the laser radiation conductive fiber, which forms the emission surface, is arranged at a region of the wall of the hollow needle opposite to the lateral emergence opening and situated at a greater distance from the lateral emergence opening than the longitudinal axis (A).

16. The applicator as claimed in claim 1, wherein:
the lateral emergence opening, as seen along the longitudinal axis (A) of the hollow needle, is arranged between, on the one hand, the closed-off end of the hollow needle and, on the other hand, the emission surface of the laser radiation emitter at the free end of the laser radiation conductive fiber.

17. The applicator as claimed in claim 1, wherein the emergence opening is produced by a chip-removing drilling through the wall of the hollow needle from the outside by means of a drill with a drilling direction aligned perpendicular to the longitudinal axis (A).

18. The applicator as claimed in claim 1, wherein:
a transition between two segments of the hollow needle which respectively have a constant but mutually different diameter is formed by an intermediate segment; and
the intermediate segment conically tapers towards the closed-off end.

19. The applicator as claimed in claim 1, wherein the laser radiation emitter comprises:
a laser radiation conductive fiber, wherein:
the laser radiation conductive fiber is attached to the wall of the hollow needle in an axial first segment of the hollow needle which contains the closed-off first end; and
the laser radiation conductive fiber is not attached to the wall of the hollow needle in an axial second segment of the hollow needle nor in an intermediate segment formed between the axial first and second segments.

20. The applicator as claimed in claim 1, wherein:
- an axial first segment, containing the closed-off end, of the hollow needle has a first diameter; and
- an axial second segment, containing a second opposite end, of the hollow needle has a greater external diameter than the first diameter.

* * * * *